US009487456B2

(12) United States Patent
Overett et al.

(10) Patent No.: US 9,487,456 B2
(45) Date of Patent: Nov. 8, 2016

(54) TETRAMERISATION OF ETHYLENE

(71) Applicant: Sasol Technology (Proprietary) Limited, Rosebank (ZA)

(72) Inventors: Matthew James Overett, Johannesburg (ZA); Munaka Christopher Maumela, Sasolburg (ZA); Moses Mokgolela Mogorosi, Sasolburg (ZA); Hulisani Maumela, Johannesburg (ZA); Molise Stephen Mokhadinyana, Sasolburg (ZA)

(73) Assignee: SASOL TECHNOLOGY (PROPRIETARY) LIMITED, Rosebank (ZA)

( * ) Notice: Subject to any disclaimer, the term of this patent is extended or adjusted under 35 U.S.C. 154(b) by 85 days.

(21) Appl. No.: 14/399,092

(22) PCT Filed: May 8, 2013

(86) PCT No.: PCT/IB2013/053699
§ 371 (c)(1),
(2) Date: Nov. 5, 2014

(87) PCT Pub. No.: WO2013/168106
PCT Pub. Date: Nov. 14, 2013

(65) Prior Publication Data
US 2015/0087873 A1 Mar. 26, 2015

Related U.S. Application Data

(60) Provisional application No. 61/644,676, filed on May 9, 2012.

(51) Int. Cl.
*C07C 2/38* (2006.01)
*C07C 2/36* (2006.01)
*B01J 31/14* (2006.01)
*B01J 31/18* (2006.01)

(52) U.S. Cl.
CPC ............... *C07C 2/36* (2013.01); *B01J 31/143* (2013.01); *B01J 31/188* (2013.01); *B01J 2231/20* (2013.01); *B01J 2531/62* (2013.01); *C07C 2531/14* (2013.01); *C07C 2531/24* (2013.01); *C07C 2531/34* (2013.01); *Y02P 20/52* (2015.11)

(58) Field of Classification Search
CPC ... C07C 2/36; C07C 11/107; C07C 2531/14; C07C 2531/24; C07C 2531/34; C97C 11/02; B01J 31/143; B01J 31/188; B01J 2231/34; B01J 2531/62; Y02P 20/52
See application file for complete search history.

(56) References Cited

U.S. PATENT DOCUMENTS

| | | | |
|---|---|---|---|
| 7,829,749 B2 † | 11/2010 | Gao | |
| 7,994,363 B2 † | 8/2011 | Gao | |
| 2006/0293546 A1 † | 12/2006 | Nabika | |
| 2011/0257350 A1 * | 10/2011 | Jaber et al. | C08F 10/00 526/145 |
| 2015/0080629 A1 * | 3/2015 | Overett et al. | C07C 2/36 585/513 |

FOREIGN PATENT DOCUMENTS

| | | |
|---|---|---|
| WO | 2004/056478 A1 † | 7/2004 |
| WO | 2004/056480 A1 † | 7/2004 |
| WO | WO 2011/130822 A1 | 10/2011 |
| WO | WO 2011/140629 A1 | 11/2011 |
| WO | WO 2012/045147 A1 | 4/2012 |

OTHER PUBLICATIONS

S. Kim et al., "Bimetallic Ethylene Tetramerization Catalysts Derived from Chiral DPPDME Ligands: Syntheses, Structural Characterizations, and Catalytic Performance of [(DPPDME)CrCl$_3$]$_2$ (DPPDME=$S,S$- and $R,R$-chlraphos and *meso*-achiraphos)", Organometallics, vol. 29, No. 22, pp. 5805-5811 (2010).
International Search Report from the European Patent Office for International Application No. PCT/IB2013/053699 mailed Aug. 29, 2013.
Written Opinion from the European Patent Office for International Application No. PCT/IB2013/053699 mailed May 9, 2014.
Hoffmann Eitle/Dr. Peter Klusmann; Opposition against EP 2 139 906 B1; Patentee: Sasol Technology (PTY) Ltd.; Oct. 7, 2014.†

* cited by examiner
† cited by third party

*Primary Examiner* — Nathan M Nutter
(74) *Attorney, Agent, or Firm* — Finnegan Henderson Farabow Garrett & Dunner LLP

(57) ABSTRACT

A process for the tetramerisation of ethylene under solution phase conditions is carried out in the presence of an activated catalyst at a temperature above 80° C. and up to a temperature of about 130° C. The activated catalyst is provided by combining a source of chromium, a ligating compound, which ligating compound includes at least one fluorine substituted hydrocarbyl group, organoheteryl group, or heterohydrocarbyl group, and optionally a catalyst activator or combination of catalyst activators.

18 Claims, No Drawings

TETRAMERISATION OF ETHYLENE

TECHNICAL FIELD

This invention relates to the tetramerisation of ethylene, in particular in the presence of an activated tetramerisation catalyst under high temperature conditions.

BACKGROUND OF THE INVENTION

It is known that chromium-based catalyst systems with diphosphine ligands catalyse the selective conversion of ethylene to 1-hexene and/or 1-octene, depending on the reaction conditions and choice of ligand structure. In particular, the nature and position of any substituents on the aryl rings connected to the phosphines are crucial influences on the selectivity towards tetramerisation of ethylene. By tetramerisation it is meant that at least 30% 1-octene is produced in the process.

Non-limiting examples of selective ethylene tetramerisation catalyst systems include the ubiquitous Cr/bis(phosphino)amine (i.e. 'PNP') systems, beginning with PNP ligands containing no substituents on the phenyl rings bonded to the P-atoms (e.g. as described in WO 2004/056479) and those with m or- p-methoxy groups on the phenyl rings (e.g. as described in WO 2004/056480). In addition to this, PNP systems containing o-fluoro groups on the phenyl rings are described in US 2008/0242811 and US 2010/008177, and PNP systems bearing pendant donor atoms on the nitrogen linker are described in WO 2007/088329. Multi-site PNP ligands are discussed in US 2008/0027188. In addition to the Cr/PNP systems, chromium systems bearing N,N-bidentate ligands (e.g. as described in US 2006/0247399) can be used. PNP ligands with alkylamine or phosphinoamine groups bonded to one of the PNP phosphines (i.e. 'PNPNH' and 'PNPNP' ligands) are described in WO 2009/006979. Finally, carbon bridged diphosphine (i.e. 'PCCP' ligands) are described in WO 2008/088178 and WO 2009/022770.

A serious drawback for tetramerisation catalysts generally is the low catalyst activity when operated at elevated temperatures, especially above 80° C. This may be explained in some cases by catalyst deactivation at elevated temperatures as described in Applied Catalysis A: General 306 (2006) 184-191.

In a recent review article describing catalyst systems for ethylene tetramerisation, van Leeuwen at al (Coordination Chemistry Reviews, 255, (2011), 1499-1517) have discussed the problems associated with elevated reaction temperatures. They state that "In general the selective ethylene tetramerisation experiments are performed in the temperature range 40-60° C. Various studies on both semi-batch and continuous miniplant have shown a strong dependency of the reaction temperature on the activity and selectivity of the Cr(III)/Ph$_2$N(R)PPh$_2$/MAO catalytic system. High reaction temperatures (>60° C.) significantly reduced the catalyst productivity as compared to reactions performed at lower temperature under the same ethylene pressure . . . . Consequently catalyst decomposition with increasing temperature is probably the main reason for lower productivities at high temperatures . . . ."

When carrying out a process for tetramerisation of ethylene, the aim is to choose a catalyst system and adjust process conditions in order to produce the maximum amount of 1-octene, as opposed to trimerisation processes where catalysts and process conditions are adjusted to produce the maximum amount of 1-hexene. 1-Hexene is also typically co-produced in a tetramerisation process and it is well known in the art of the invention that higher temperatures shift the selectivity from 1-octene towards 1-hexene. This is a further issue to consider when operating a tetramerisation process at higher temperatures.

Furthermore, the formation of a high molecular weight polymer co-product by the Cr-based ethylene tetramerisation catalyst may present a major technical challenge when commercialising an ethylene tetramerisation process as polymer fouling reduces plant run time and necessitates shut-downs due to blockages and difficult temperature control. When running tetramerisation processes at reaction temperatures in the range of 40 to 80° C., the polymer precipitates out of solution in the reactor, which brings risk to the process due to the possibility of reactor or downstream equipment fouling.

SUMMARY OF THE INVENTION

According to one aspect of the invention there is provided a process for the tetramerisation of ethylene, the process including:
(a) providing an activated catalyst comprising:
   i) a source of chromium;
   ii) a ligating compound of the formula $R^1R^2P^1XP^2R^3R^4$ wherein $P^1$ and $P^2$ are phosphorus atoms;
   X is a linking group between $P^1$ and $P^2$; and
   $R^1$ to $R^4$ are independently a hydrocarbyl group, an organoheteryl group or a heterohydrocarbyl group, wherein at least one of $R^1$, $R^2$, $R^3$, and $R^4$ contains a fluorine substituent and
   iii) optionally a catalyst activator or combination of catalyst activators; and
(b) contacting ethylene to be tetramerised with the activated catalyst at a reaction temperature of from above 80° C. to about 130° C.

In some embodiments of the Invention the ethylene is contacted with the activated catalyst at a reaction temperature of from above 85° C. to about 120° C.

In some embodiments of the invention the ethylene is contacted with the activated catalyst at a reaction temperature of from above 90° C. to about 110° C.

DETAILED DESCRIPTION OF EMBODIMENTS OF THE INVENTION

The invention relates to a process for the tetramerisation of ethylene under solution phase conditions. The process is carried out in the presence of an activated catalyst at a temperature above 80° C. and up to a temperature of about 130° C. The activated catalyst is provided by combining a source of chromium, a ligating compound, which ligating compound includes at least one fluorine substituted hydrocarbyl group, organoheteryl group, or heterohydrocarbyl group, and optionally a catalyst activator or combination of catalyst activators.

In the specification, the following definitions apply:
A "hydrocarbyl group" as per IUPAC includes a univalent group formed by removing one hydrogen atom from a hydrocarbon;
A "heterohydrocarbyl group" as defined herein is a univalent group formed by removing one hydrogen atom from a carbon atom of a heterohydrocarbon, that is a hydrocarbon compound which includes at least one hetero atom (that is, not being H or C), and which group covalently bonds with one other moiety through the resultant free valency on that carbon atom;

An "organoheteryl group" as per IUPAC includes univalent groups containing carbon, which are thus organic, but which have their free valence at an atom other than carbon;

A "hydrocarbylene group" as per IUPAC includes divalent groups formed by removing two hydrogen atoms from a hydrocarbon, the free valencies of which are not engaged in a double bond;

A "heterohydrocarbylene group" as defined herein is a divalent group formed by removing two hydrogen atoms from either one or two carbon atoms of an organic molecule containing at least one heteroatom, the free valencies of which are not engaged in a double bond.

Chromium Source (i):

Any source of chromium that allows the oligomerisation to proceed may be used. The source of chromium may be an inorganic salt, an organic salt, a coordination compound or an organometallic complex.

In some embodiments the source of chromium is selected from the group consisting of chromium trichloride tristetrahydrofuran complex; (benzene)tricarbonyl chromium; chromium (III) octanoate; chromium hexacarbonyl; chromium (III) acetylacetonate: chromium (III) naphthenate; chromium (III) 2-ethylhexanoate; chromium (III) acetate; chromium (III) 2,2,6,6-tetramethyiheptadionate; and chromium (III) chloride. In some embodiments it is chromium (III) acetylacetonate or chromium (III) 2-ethylhexanoate.

The chromium source may be introduced to the process as a coordination complex of the ligating compound. However, for reasons of cost and commercial operability, in some embodiments the ligating compound and chromium source are added as separate components to the process. Catalyst systems which give good catalyst performance only when an isolable chromium-ligand coordination complex is used therefore suffer a disadvantage to catalyst systems which can be prepared by mixing a chromium source and ligand in the process.

Ligating Compound (ii):

Linking Group X

X may be selected from the group consisting of an organic linking group such as a hydrocarbylene, heterohydrocarbylene; an inorganic linking group comprising either a single- or two-atom linker spacer; and a group comprising dimethylmethylene, ethane-1,2-diyl, ethene-1,2-diyl, propane-1,2-diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracenediyl, 1,2-catecholate, 1,2-diarylhydrazine-1,2-diyl (—N(Ar)—N(Ar)- where Ar is an aryl group), 1,2-dialkylhydrazine-1,2-diyl (—N(Alk)-N(Alk)- where Alk is an alkyl or a cycloalkyl group), 1-alkyl-2-arylhydrazine-1,2-diyl (—N(Alk)-N(Ar)- where Alk is an alkyl or a cycloalkyl group and Ar is an aryl group), —N(R')—X$^1$—N(R")— where R' and R" are independently alkyl, cycloalkyl or aryl groups and X$^1$ is a hydrocarbylene group, —B(R$^5$)—, —Si(R$^5$)$_2$—, —P(R$^5$)— and —N(R$^5$)— where R$^5$ is hydrogen, a hydrocarbyl group, an organoheteryl group or a heterohydrocarbyl group. Preferably R$^5$ is a hydrocarbyl group or a heterohydrocarbyl group.

In some embodiments X consists of —N(R$^6$)—, —N(R$^6$)—N(R$^7$)—, —C(R$^{8a}$)(R$^{8b}$)—N(R$^6$)— or a hydrocarbylene, where R$^6$ and R$^7$ are independently a hydrocarbyl group, a heterohydrocarbyl group or an organohetery group, and R$^{8a}$ and R$^{8b}$ are independently a hydrogen, a hydrocarbyl group, a heterohydrocarbyl group or an organoheteryl group. In some embodiments R$^6$, R$^7$, R$^{8a}$ and R$^{8b}$ may be an alkyl, cycloalkyl, substituted alkyl, substituted cycloalkyl, aryl, substituted aryl, aryloxy, substituted aryloxy, alkoxycarbonyl, carbonyloxy, alkoxy, aminocarbonyl, carbonylamino, dialkylamino, pyrolyl, silyl group or derivative thereof, and aryl substituted with any of these substituents, and R$^{8a}$ and R$^{8b}$ may additionally be hydrogen. In some embodiments R$^6$, R$^7$, R$^{8a}$ and R$^{8b}$ may be an alkyl, cycloalkyl, substituted alkyl, substituted cycloalkyl, aryl, substituted aryl, dialkylamino, silyl group or derivative thereof, and R$^{8a}$ and R$^{8b}$ may additionally be hydrogen. In some embodiments, R$^6$, R$^7$, R$^{8a}$ and R$^{8b}$ consist of hydrocarbyl groups, such as methyl, ethyl, propyl, allyl, isopropyl, cyclopropyl, butyl, tertiary-butyl, sec-butyl, cyclobutyl, pentyl, isopentyl, 1,2-dimethylpropyl (3-methyl-2-butyl), 1,2,2-trimethylpropyl (R/S-3,3-dimethyl-2-butyl), 1-(1-methylcyclopropyl)-ethyl, neopentyl, cyclopentyl, cyclohexyl, hexyl, cycloheptyl, cyclo-octyl, decyl, cyclodecyl, 1,5-dimethylheptyl, 1-methylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, (1,1'-bis(cyclohexyl)-4,4'-methylene), 1,6-hexylene, 1-naphthyl, 2-naphthyl, diphenylmethyl, 1,2-diphenyl-ethyl, phenylethyl, 2-methylphenyl, 3-methylphenyl, 4-methylphenyl, 2,6-dimethyl-phenyl, or a 1,2,3,4-tetrahydronaphthyl, and R$^{8a}$ and R$^{8b}$ may additionally be hydrogen.

In a preferred embodiment X is a hydrocarbylene, —N(R$^5$)—, —N(R$^5$)—N(R$^6$)—, —N(R$^5$)—C(R$^7$)(R$^8$)—, N(R$^5$)—X$^1$—N(R$^6$) where R$^5$ and R$^6$ are independently a hydrocarbyl group, an organoheteryl group or a heterohydrocarbyl group, R$^7$ and R$^8$ are independently a hydrogen, a hydrocarbyl group, an organoheteryl group or a heterohydrocarbyl group, and X$^1$ is a hydrocarbylene group.

In some embodiments, X is —N(R$^9$)—, where R$^9$ is a hydrocarbyl group, a heterohydrocarbyl group or an organoheteryl group. In some embodiments R$^9$ is a hydrocarbyl group or a heterohydrocarbyl group. In some embodiments R$^9$ is an alkyl, cycloalkyl or aryl group. In some embodiments R$^9$ is an alkyl or cycloalkyl group. In some embodiments R$^9$ is an alkyl group of the form —CH$_2$R$^{10}$, where R$^{10}$ is hydrogen or an alkyl group or a cycloalkyl group. In some embodiments R$^9$ is methyl or a linear alkyl group.

Nature of the Groups R$^1$-R$^4$

R$^1$ to R$^4$ are independently a hydrocarbyl, an organoheteryl group or a heterohydrocarbyl group, such that at least one of R$^1$, R$^2$, R$^3$, and R$^4$ contains a fluorine substituent. In some embodiments, R$^1$ to R$^4$ are independently a hydrocarbyl or a heterohydrocarbyl group, such that at least one of R$^1$, R$^2$, R$^3$, and R$^4$ contains a fluorine substituent. In some embodiments at least one of R$^1$ to R$^4$ is an aromatic moiety or a heteroaromatic moiety directly bonded to P$^1$ or P$^2$. In some embodiments R$^1$ to R$^4$ are all aromatic or heteroaromatic moieties directly bonded to P$^1$ or P$^2$. In some embodiments R$^1$ to R$^4$ are all aromatic moieties directly bonded to P$^1$ or P$^2$. In some embodiments R$^1$ to R$^4$ are optionally substituted phenyl groups.

Nature of One or More Fluorinated Groups R$^1$-R$^4$

In some embodiments of the invention, one or more of the R$^1$ to R$^4$ groups containing a fluorine substituent are fluorine-substituted hydrocarbyl, heterohydrocarbyl or organoheteryl groups.

In some embodiments one or more of the $R^1$ to $R^4$ groups containing a fluorine substituent are either aromatic, including heteroaromatic, moieties directly bonded to $P^1$ or $P^2$ and containing a fluorine atom or a fluorinated substituent at a ring atom of the aromatic ring structure that is no more than two atoms away along the shortest connecting path from the ring atom bound to $P^1$ or $P^2$, or are groups containing aromatic, including heteroaromatic, moieties separated from $P^1$ or $P^2$ by a single atom linker, which contain a fluorine atom or a fluorinated substituent at a ring atom of the aromatic ring structure that is no more than two atoms away along the shortest connecting path from the ring atom bound to the single atom linker.

Examples of suitable fluorinated substituents include, but are not limited to, fluoromethyl, difluoromethyl, trifluoromethyl, 1-fluoroethyl, 2-fluoroethyl, 2-fluorophenyl and the like.

In some embodiments one or more of the $R^1$ to $R^4$ groups containing a fluorine substituent are aromatic, including heteroaromatic, moieties directly bonded to $P^1$ or $P^2$ and containing a fluorine atom or a fluorinated substituent at a ring atom of the aromatic ring structure that is no more than two atoms away along the shortest connecting path from the ring atom bound to $P^1$ or $P^2$.

In some embodiments one or more of the $R^1$ to $R^4$ groups containing a fluorine substituent are aromatic moieties directly bonded to $P^1$ or $P^2$ and containing a fluorine atom or fluorinated substituent at a ring atom of the aromatic ring structure that is no more than two atoms away along the shortest connecting path from the ring atom bound to $P^1$ or $P^2$.

In some embodiments one or more of the $R^1$ to $R^4$ groups containing a fluorine substituent are aromatic moieties directly bonded to $P^1$ or $P^2$ and containing a fluorine atom at a ring atom of the aromatic ring structure that is no more than two atoms away along the shortest connecting path from the ring atom bound to $P^1$ or $P^2$.

In some embodiments one or more of the $R^1$ to $R^4$ groups containing a fluorine substituent are aromatic moieties directly bonded to $P^1$ or $P^2$ and containing a fluorine atom or fluorinated substituent at a ring atom of the aromatic ring structure that is adjacent to the ring atom bound to $P^1$ or $P^2$.

In some embodiments one or more of the $R^1$ to $R^4$ groups containing a fluorine substituent are aromatic moieties directly bonded to $P^1$ or $P^2$ and containing a fluorine atom at a ring atom of the aromatic ring structure that is adjacent to the ring atom bound to $P^1$ or $P^2$.

In some embodiments one or more of the $R^1$ to $R^4$ groups containing a fluorine substituent are selected from the group consisting of optionally substituted 2-fluorophenyl groups, optionally substituted 2-fluoronaphth-1-yl groups, optionally substituted 1-fluoronaphth-2-yl groups, optionally substituted 3-fluoronaphth-2-yl groups, optionally substituted 8-fluoronaphth-1-yl groups, optionally substituted 2-fluoropyrid-3-yl groups, optionally substituted 3-fluoropyrid-2-yl groups, optionally substituted 3-fluoropyrid-4-yl groups, optionally substituted 4-fluoropyrid-3-yl groups, optionally substituted 2-fluorofuran-3-yl groups, optionally substituted 3-fluorofuran-2-yl groups, optionally substituted 4-fluorofuran-3-yl groups, optionally substituted 2-fluorothiophen-3-yl groups, optionally substituted 3-fluorothiophen-2-yl groups, optionally substituted 4-fluorothiophen-3-yl groups, optionally substituted 2-fluoropyrrol-1-yl groups, optionally substituted 3-fluoropyrrol-2-yl groups, optionally substituted 2-fluoropyrrol-3-yl groups and optionally substituted 4-fluoropyrrol-3-yl groups.

In some embodiments one or more of the $R^1$ to $R^4$ groups containing a fluorine substituent are selected from the group consisting of optionally substituted 2-fluorophenyl groups and optionally substituted 8-fluoronaphth-1-yl groups.

In some embodiments one or more of the $R^1$ to $R^4$ groups containing a fluorine substituent are optionally substituted 2-fluorophenyl groups.

Number and Substitution Pattern of the Fluorinated Groups $R^1$-$R^4$ $R^1$ to $R^4$ are independently a hydrocarbyl group, an organoheteryl group or a heterohydrocarbyl group, such that at least one of $R^1$, $R^2$, $R^3$, and $R^4$ contains a fluorine substituent. In some embodiments no more than two of $R^1$ to $R^4$ contain a fluorine substituent. In some embodiments, $R^1$ and $R^2$ both contain a fluorine substituent. In some embodiments, only $R^1$ contains a fluorine substituent, while $R^2$, $R^3$ and $R^4$ do not contain fluorine substituents.

Other Considerations

Any one of $R^1$ to $R^4$ may independently be linked to one or more of each other, or to X, to form a cyclic structure.

The ligating compound may also include multiple $R^1R^2P^1XP^2R^3R^4$ units. Non-limiting examples of such ligands include dendrimeric ligands as well as ligands where the individual units are coupled either via one or more of the $R^1$—$R^4$ groups or via the linking group X.

It will be appreciated that a diphosphinoimine compound of the form $R^1R^2P^1$—$P^2(=NR^9)R^3R^4$ ('P—P=N') is a rearranged isomer of the diphosphinoamine compound $R^1R^2P^1N(R^9)P^2R^3R^4$ ('P—N—P') claimed in the present invention, as shown by Dyson et al in Inorganica Chimica Acta 359 (2006) 2635-2643.

Regardless of the structural formulation of the ligating compound in its pure and Isolated form, its use will fall under the present Invention if it exists in the 'P—N—P' form when used in a tetramerisation process.

In some embodiments the ligating compound may be one of (2-fluorophenyl)$_2$PN(hydrogen)P(phenyl)$_2$; (2-fluorophenyl)$_2$PN(methyl)P(phenyl)$_2$; (2-fluorophenyl)$_2$PN(n-butyl)P(phenyl)$_2$; (2-fluorophenyl)$_2$PN(n-hexyl)P(phenyl)$_2$; (2-fluorophenyl)$_2$PN(n-decyl)P(phenyl)$_2$; (2-fluorophenyl)$_2$PN(isobutyl)P(phenyl)$_2$; (2-fluorophenyl)$_2$PN(isopropyl)P(Phenyl)$_2$; (2-fluorophenyl)$_2$PN(isopentyl)P(phenyl)$_2$; (2-fluorophenyl)$_2$PN(t-butyl)P(phenyl)$_2$; (2-fluorophenyl)$_2$PN(1,2-dimethylpropyl)P(phenyl)$_2$; (2-fluorophenyl)$_2$PN(cyclopropyl)P(phenyl)$_2$; (2-fluorophenyl)$_2$PN(cyclopropylmethyl)P(phenyl)$_2$; (2-fluorophenyl)$_2$PN(allyl)P(phenyl)$_2$; (2-fluorophenyl)$_2$PN(trimethylsilyl)P(phenyl)$_2$; (2-fluorophenyl)$_2$PN(pyrollyl)P(phenyl)$_2$; (2-fluorophenyl)$_2$PN(phenyl)P(phenyl)$_2$; (2-fluorophenyl)$_2$PN(naphthyl)P(phenyl)$_2$; (2-fluorophenyl)$_2$PN(methylmorpholine)P(phenyl)$_2$; (2-fluorophenyl)$_2$PN(dimethylamino)P(phenyl)$_2$; (2-fluorophenyl)$_2$PN(benzyl)P(phenyl)$_2$; (2-fluorophenyl)(phenyl)PN(methyl)P(2-fluorophenyl)(phenyl); (2-fluorophenyl)(phenyl)PN(n-hexyl)P(2-fluorophenyl)(phenyl); (2-fluorophenyl)(phenyl)PN(n-decyl)P(2-fluorophenyl)(phenyl); (2-fluorophenyl)(phenyl)PN(isobutyl)P(2-fluorophenyl)(phenyl); (2-fluorophenyl)(phenyl)PN(isopropyl)P(2-fluorophenyl)(phenyl); (2-fluorophenyl)(phenyl)PN(1,2-dimethylpropyl)P(2-fluorophenyl)(phenyl); (2-fluorophenyl)(phenyl)PN(cyclopropyl)P(2-fluorophenyl)(phenyl); (2-fluorophenyl)(phenyl)PN(trimethylsilyl)P(2-fluorophenyl)(phenyl); (2-fluorophenyl)(phenyl)PN(phenyl)P(2-fluorophenyl)(phenyl); (2-fluorophenyl)$_2$PN(methyl)P(2-fluorophenyl)$_2$; (2-fluorophenyl)$_2$PN(n-butyl)P(2-fluorophenyl)$_2$; (2-fluorophenyl)$_2$PN(n-hexyl)P(2 fluorophenyl)$_2$; (2-fluorophenyl)$_2$PN(n-decyl)P(2-fluorophenyl)$_2$; (2 fluorophenyl)$_2$PN(isobutyl)P(2-fluorophenyl)$_2$;

(2-fluorophenyl)₂PN(isopentyl)P(2-fluorophenyl)₂; (2-fluorophenyl)₂PN(cyclopropyl)P(phenyl)₂; (2-fluorophenyl)₂PN(trimethylsilyl)P(2-fluorophenyl)₂; (2 fluorophenyl)₂PN(phenyl)P(2-fluorophenyl)₂; (2 fluorophenyl)₂PN(benzyl)P (2 fluorophenyl)₂; (2-fluorophenyl)(phenyl)PN(methyl)P (phenyl)₂; (2-fluorophenyl)(phenyl)PN(n-decyl)P(phenyl)₂; (2-fluorophenyl)(phenyl)PN(isobutyl)P(phenyl)₂; (2-fluorophenyl) (phenyl) PN (isopropyl)P(phenyl)₂; (2-fluorophenyl)(phenyl)PN(trimethylsilyl)P(phenyl)₂; (2-fluorophenyl)(phenyl)PN(benzyl)P(phenyl)₂; (2-fluorophenyl)(phenyl)PN(phenyl)P(phenyl)₂; (2-fluorophenyl)(phenyl)PN(methylmorpholine)P(phenyl)₂; (2-fluoronaphth-1-yl)₂PN(methyl)P(phenyl)₂; (1-fluoronaphth-2-yl)₂PN(methyl)P(phenyl)₂; (2-fluoronaphth-1-yl)₂PN(n-butyl)P(phenyl)₂; (1-fluoronaphth-2-yl)₂PN(n-hexyl)P(phenyl)₂; (2-fluoronaphth-1-yl)(phenyl)PN(n-butyl)P(phenyl)₂; (1 fluoronaphth-2-yl)(phenyl)PN(n-hexyl)P(phenyl)₂; (2-fluoronaphth-1-yl)₂PN(n-decyl)P(phenyl)₂; (1-fluoronaphth-2-yl)₂PN (isobutyl)P(phenyl)₂; (8-fluoronaphth-1-yl)₂PN(isopropyl)P(phenyl)₂; (8-fluoronaphth-1-yl)₂PN(n-hexyl)P(phenyl)₂; (8-fluoronaphth-1-yl)₂PN(methyl)P(phenyl)₂; (8-fluoronaphth-1-yl)₂PN (phenyl)P(Phenyl)₂; (8-fluoronaphth-1-yl)₂PN(cyclopropyl)P(phenyl)₂; (8-fluoronaphth-1-yl)₂PN(benzyl)P(phenyl)₂; (8-fluoronaphth-1-yl) (phenyl)PN(n-hexyl)P(phenyl)₂; (8-fluoronaphth-1-yl) (phenyl)PN(isopropyl)P(phenyl)₂; (8-fluoronaphth-1-yl)₂PN(trimethylsilyl)P(phenyl)₂; (3-fluoronaphth-2-yl)₂PN(hexyl)P(Phenyl)₂; (3-fluoronaphth-2-yl)₂PN(isopropyl)P(phenyl)₂; (3-fluoronaphth-2-yl)(phenyl)PN(hexyl)P(phenyl)₂; (3-fluoronaphth-2-yl)(phenyl)PN(isopropyl)P(phenyl)₂ (3-fluoropyrid-4-yl)₂PN(methyl)P(phenyl)₂; (3-fluoropyrid-4-yl)₂PN(n-butyl)P(phenyl)₂; (4-fluoropyrid-3-yl)₂PN(n-butyl)P(phenyl)₂; (3-fluoropyrid-2-yl)₂PN(n-butyl)P(phenyl)₂; (2-fluoropyrid-3-yl)₂PN(n-butyl)P(phenyl)₂; (3-fluoropyrid-4-yl)(phenyl)PN(n-buty)P(Phenyl)₂; (3-fluoropyrid-4)(phenyl)PN(n-butyl)P(3-fluoropyrid-4-yl)₂; (4-fluoropyrid-3-yl)(phenyl)PN(n-butyl)P(phenyl)₂; (4-fluoropyrid-3-yl)₂PN(n-butyl)P(4-fluoropyrid-3-yl)₂; (3-fluoropyrid-2-yl)₂PN(n-butyl)P(phenyl)₂; (3-fluoropyrid-2-yl)₂PN(n-butyl)P(3-fluoropyrid-2-yl)₂; (2-fluoropyrid-3-yl)(phenyl)PN(n-butyl)P(phenyl)₂; (2-fluoropyrid-3-yl)₂PN(n-butyl)P(2-fluoropyrid-3-yl)₂; (3-fluorofuran-2-yl)₂PN(n-butyl)P(phenyl)₂; (2-fluorofuran-3-yl)₂PN(n-butyl)P(phenyl)₂; (3-fluorofuran-4-yl)₂PN(n-butyl)P(phenyl)₂; (3-fluorofuran-2-yl)(phenyl)PN(n-butyl)P(phenyl)₂; (2-fluorofuran-3-yl)(phenyl)PN(n-butyl)P(phenyl)₂; (3-fluorofuran-4-yl)(phenyl)PN(n-butyl)P(phenyl)₂; (3-fluorofuran-2-yl)₂PN(n-butyl)P(3-fluorofuran-2-yl)₂; (2-fluorofuran-3-yl)₂PN(n-buty)P(2 fluorofuran-3-yl)₂; (3-fluorofuran-4-yl)₂PN(n-butyl)P(3-fluorofuran-yl)₂; (3-fluorothiophen-2-yl)₂PN(n-butyl)P(phenyl)₂; (2-fluorothiophen-3-yl)₂PN(n-butyl)P(phenyl)₂; (3-fluorothiophen-4-yl)₂PN(n-butyl)P(phenyl)₂; (3-fluorothiophen-2-yl)(phenyl)PN(n-butyl)P(phenyl)₂; (2-fluorothiophen-3-yl)(phenyl)PN(n-butyl)P(phenyl)₂; (3-fluorothiophen-4-yl)(phenyl)PN(n-butyl)P(Phenyl)₂; (3-fluorothiophen-2-yl)₂PN(n-butyl)P(3-fluorothiophen-2-yl)₂; (2-fluorothiophen-3-yl)₂PN(n-butyl)P(2-fluorothiophen-3-yl)₂; (3-fluorothiophen-4-yl)₂PN(n-butyl)P(3-fluorothiophen-4-yl)₂; (2-fluoropyrrol-1-yl)₂PN(n-butyl)P(phenyl)₂; (3-fluoropyrrol-2-yl)₂PN(n-butyl)P(phenyl)₂; (2 fluoropyrrol-3-yl)₂PN(n-butyl)P(phenyl)₂; (4-fluoropyrrol-3-yl)₂PN(n-butyl)P(Phenyl)₂; (2-fluoropyrrol-1-yl)(phenyl)PN(n-butyl)P(phenyl)₂; (3-fluoropyrrol-2-yl)(phenyl)PN(n-butyl)P(phenyl)₂; (2-fluoropyrrol-3-yl)(phenyl)PN(n-butyl)P(phenyl)₂; (4-fluoropyrrol-3-yl)(phenyl)PN(n-butyl)P(phenyl)₂; (5-fluoroquinol-4-yl)₂PN(n-butyl)P(phenyl)₂; (4-fluoroquinol-4-yl)₂PN(n-butyl)P(phenyl)₂; (5-fluoroquinol-4-yl)(phenyl)PN(n-butyl)P(phenyl)₂; (4-fluoroquinol-4-yl)(phenyl)PN(n-butyl)P(phenyl)₂; (2-fluorophenoxy)₂PN(n-butyl)P(phenyl)₂; (2 fluorophenoxy)(phenyl)PN(n-butyl)P(phenyl)₂; (2-[trifluoromethyl]phenyl)₂PN(n-butyl)P(phenyl)₂; (2-[trifluoromethyl]phenyl)(phenyl)PN(n-butyl)P(phenyl)₂; (2-[difluoromethyl]phenyl)₂PN (n-butyl)P(phenyl)₂; (2-[difluoromethyl]phenyl)(phenyl)PN (n-butyl)P(phenyl)₂; (2-[fluoromethyl]phenyl)₂PN (n-butyl)P(phenyl)₂; (2-[fluoromethyl]phenyl)(phenyl)PN(n-butyl)P(phenyl)₂; (2-[2-fluorophenyl]phenyl)₂PN(n-butyl)P(phenyl)₂; (2-[2-fluorophenyl]phenyl)(phenyl)PN(n-butyl)P(phenyl)₂; (2-fluorophenyl)₂PN(n-butyl)P(1,2-phenylenedioxy); (2-fluorophenyl)(2-methylphenyl)PN(isopropyl)P(phenyl)₂; (2-fluorophenyl)(2-methylphenyl)PN(n-butyl)P(phenyl)₂; (2-fluorophenyl)(phenyl)PN(isopropyl)P(phenyl)(2-methylphenyl); (2-fluorophenyl)₂PN(n-hexyl)P(ethyl)₂; (2-fluorophenyl)₂PN(n-hexyl)P(ethyl)(phenyl); (2-fluoroethyl)₂PN(n-hexyl)P(phenyl)₂; (2,2,2-trifluoroethyl)₂PN(n-hexyl)P(phenyl)₂; (2-fluorophenyl)₂PCH₂CH₂P(phenyl)₂; (2-fluorophenyl)₂PN(Me)N(Me)P(phenyl)₂; (2-fluorophenyl)(phenyl)PCH₂CH₂P(phenyl)₂; (2-fluorophenyl)(phenyl)₂PN(Me)N(Me)P(phenyl)₂; (2-fluorophenyl)₂PCH₂N(naphthyl)P(phenyl)₂; (2-fluorophenyl)₂P(1,2-phenylene)P(phenyl)₂; (2-fluorophenyl)(phenyl)P(1,2-phenylene))P(phenyl)₂.

Activator/Additives (iii):

The above process may include an activator to activate the catalyst. Such an activator is a compound that generates an active catalyst when the activator is combined with the catalyst. These activators may be the same or similar to those found to be useful for activating transition-metal-based olefin polymerisation catalysts, a review of which is provided by Marks [*Chem Rev.* 2000, 100, 1391-1394]. Mixtures of activators may also be used.

Suitable compounds include organoaluminum compounds, organoboron compounds and inorganic acids and salts, such as tetrafluoroboric acid etherate, silver tetrafluoroborate, sodium hexafluoroantimonate and the like.

Suitable organoaluminum compounds include compounds of the formula AlR₃, where each R is independently $C_1$-$C_{12}$ alkyl, oxygen or halide, and compounds such as LiAlH₄ and the like. Examples include trimethylaluminum (TMA), triethylaluminum (TEA), tri-isobutylaluminium (TIBA), trl-n-octylaluminium, methylaluminium dichloride, ethylaluminium dichloride, dimethylaluminium chloride, diethylaluminium chloride, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available aluminoxanes are generally believed to be mixtures of linear and cyclic compounds. The cyclic aluminoxanes can be represented by the formula [$R^{11}$AlO]$_s$ and the linear aluminoxanes by the formula $R^{12}(R^{13}AlO)$, wherein a is a number from about 2 to 50, and wherein $R^{11}$, $R^{12}$, and $R^{13}$ represent hydrocarbyl groups, typically $C_1$ to $C_6$ alkyl groups, for example methyl, ethyl or butyl groups. Alkylaluminoxanes especially methylaluminoxane (MAO) are particularly suitable. (MAO is also referred to as methalumoxane and methylalumoxane in the literature).

It will be recognized by those skilled in the art that commercially available alkylaluminoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylaluminoxane are generally quoted herein on a molar basis of aluminium (and include such "free" trialkylaluminium). The alkylaluminoxane and/or alkylaluminium may be added to the reaction media (i.e. ethylene and/or diluent and/or solvent) prior to the addition of the catalyst or at the same time as the catalyst is added. Such techniques are known in the art of oligomerization and are disclosed in more detail in for example, U.S. Pat. Nos. 5,491,272; 5,750,817; 5,856,257; 5,910,619; and 5,919,996 as well as WO 2008/146215 and WO 2007/007272.

In the preparation of the catalyst systems used in the present invention, the optimal quantity of activating compound to be employed is easily determined by simple testing, for example, by the preparation of small test samples which can be used to oligomerize small quantities of ethylene and thus to determine the activity of the produced catalyst. It is generally found for alkylaluminium and aluminoxane based activators or co-activators that a suitable quantity employed is 0.5 to 2000 moles of aluminium per mole of chromium.

Examples of suitable organoboron activator compounds are boroxines, $NaBH_4$, trimethylboron, triethylboron, triphenylboron, dimethylphenylammoniumtetra(phenyl)borate, trityltetra(phenyl)borate, dimethylphenylammonium tetrakis(pentafluorophenyl)borate, trityl tetrakis(pentafluorophenyl)borate, tris(pentafluorophenyl) boron, sodium tetrakis[(bis-3,5-trifluoromethyl)phenyl]borate, dimethylphenylammonium tetrakis[(bis-3,5-trifluoromethyl)phenyl]borate, and trityl tetrakis[(bis-3,5-trifluoromethyl)phenyl]borate.

Those skilled in the art will recognise that boron-containing activators are commonly used in combination with aluminium alkyl activators.

In some embodiments organoboron activators, as described in WO 2010/092554, include a cation and a non-coordinating anion of the general formula

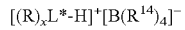

wherein:
L* is an atom selected from the group consisting of N, S and P;
the cation [(R), L*-H]⁺ is a Bronsted acid;
x is an integer 1, 2 or 3;
each R is the same or different and each is a —H, hydrocarbyl group or a heterohydrocarbyl group;
provided that at least one of R comprises at least 6 carbon atoms and provided further that the total number of carbon atoms in $(R)_x$ collectively is greater than 12;
$R^{14}$ independently at each occurrence is selected from the group consisting of hydride, dialkylamido, halide, alkoxide, aryloxide, hydrocarbyl, halosubstituted-hydrocarbyl radicals, halosubstituted-alkoxide, halosubstituted-aryloxide and a halosubstituted aromatic moiety with at least one halide substituent on the aromatic moiety.

Illustrative, but non-limiting examples of these organoboron activators include methyldi(octadecyl)ammonium tetrakis(pentafluorophenyl) borate and trioctylammonium tetrakis(pentafluorophenyl) borate.

The source of chromium and the organoboron activator may be combined in proportions to provide organoboron compound/chromium molar ratios from about 0.1 to 50 organoboron to 1 chromium, or from about 0.8 to 20 organoboron to 1 chromium, or from 1 to 10 organoboron to 1 chromium.

In some embodiments activators, as described in WO 2007/039851, include a cation and an anion component, and may be represented by the following formula:

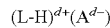

where L is a neutral Lewis base; H is hydrogen; $(L-H)^{d+}$ is a Bronsted acid; $A^{d-}$ is a non-coordinating anion having the charge d⁻; and d is an integer from 1 to 3.

In these activator compounds, $A^{d-}$ can be a fluorinated aluminate group. Illustrative but non-limiting examples of the anion component $A^{d-}$ are $[Al\{OC(CF_3)_3\}_4]^-$; $[Al(OC_6F_5)_4]^-$; $[Al(C_6F_4O_2)_2]^-$; $[AlF\{OC(CF_3)_3\}_3]^-$; $[Al_2F\{OC(CF_3)_3\}_3]^-$; and $[Ta(OC_6F_5)_6]^-$.

The activator compound may optionally be a solid material, or be supported on an insoluble solid material. For example, aluminoxanes such as MAO and borate activators may be supported on inorganic oxides such as alumina, silica, $MgCl_2$ or the like.

The process may further include the use of compounds that may act as a reducing or oxidising agent, such as sodium or zinc metal and the like, or an oxygen-containing compound, for example oxygen and the like. Additionally, hydrogen ($H_2$) and/or silanes and the like may be used in the catalytic composition or otherwise added to the process. The process may also include the use of a zinc species as an additive, as described in WO 2011/048527, which is herein incorporated by reference. Preferred zinc species would be dialkyl zinc reagents such as dimethylzinc or diethylzinc.

Catalyst Preparation:

The chromium (i) and ligand (ii) may be present in any molar ratio which produces oligomer, and in some embodiments is between 100:1 and 1:100, or from 10:1 to 1:10, or from 3:1 to 1:3. Generally the amounts of (i) and (ii) are approximately equal, i.e. a ratio of between 1.5:1 and 1:1.5.

The ligand, chromium and activators of the catalyst system utilized in the present invention may be added together simultaneously or sequentially, in any order, and in the presence or absence of ethylene or other unsaturated hydrocarbon in any suitable solvent at any suitable concentration, so as to give an active catalyst. For example, the ligand, chromium, activators and ethylene may be contacted together simultaneously; or the ligand, chromium and activators may be added together simultaneously or sequentially in any order and then contacted with ethylene; or chromium and the ligand may be added together to form an isolable metal-ligand complex and then added to the activator and contacted with ethylene; or the ligand, chromium and activators/co-activators may be added together to form an isolable metal-ligand complex and then contacted with ethylene.

Any or all of the chromium source, ligating compound and activator components utilized in the present invention can be unsupported or supported on a support material, for example silica, alumina, $MgCl_2$ or zirconia, or on a polymer, for example polyethylene, polypropylene, polystyrene or poly(aminostyrene).

Diluent:

The process of the present invention may be carried out in the presence or absence of an added diluent. In some embodiments of the invention the diluents include oligomerisation products e.g. 1-octene and/or 1-hexene, aliphatic and aromatic hydrocarbon solvents, aliphatic substituted aromatic solvents and halogenated-aromatic solvents such as chlorobenzene, dichlorobenzene, fluorobenzene and the like. In some embodiments the diluents are aliphatic hydrocarbon solvents including but not limited to Isopar™, iso-octane, cyclohexane, cyclopentane, methylcyclohexane, propane, isobutane, isopentane, neopentane, 2-methylpentane, or 3-methylpentane.

Alternatively the process can be conducted as a bulk process in which essentially neat reactant and/or product olefins serve as the dominant medium.

Process Conditions:

The tetramerization may be conducted under solution phase conditions, which is herein taken to mean that any polymer co-product remains substantially dissolved in the liquid reaction medium under the chosen reaction conditions. Suitable temperatures to achieve this range from above 80° C. to about 130° C. In some embodiments the temperature range is between 85° C. and 120° C., preferably 85° C. to about 100° C., whilst in other embodiments the temperature range is between 90° C. and 110° C. In some embodiments the temperature range is from above 80° C. or above 85° C. or above 90° C. to about 130° C. or about 120° C. or about 115° C. or about 110° C. or about 100° C. or about 105° C. or about 100° C.

The formation of a high molecular weight polymer co-product by the Cr-based ethylene tetramerisation catalyst may present a major technical challenge when commercialising an ethylene tetramerisation process. Polymer fouling of the reactor or downstream sections will reduce plant run time and necessitate shut-downs due to blockages and loss of reaction cooling due to coating of heat exchange surfaces. When running tetramerisation processes at reaction temperatures in the range of 40 to 80° C., as is taught in the art, most of the polymer co-product precipitates in the reactor, which can result in fouling of process equipment. To ensure process reliability and adequate run-times under such reaction conditions, it may be necessary to utilise expensive or energy-intensive process design features.

Running a tetramerisation process at process conditions whereby the polymer co-product remains predominantly dissolved in the liquid reaction medium in the reactor (i.e. a solution phase process) would substantially reduce the possibility of reactor or downstream fouling. In addition, a further benefit of such a process might be that a cheaper or more energy-efficient process design could be used, due to the reduced likelihood of fouling process equipment. A solution phase process could be achieved by using higher reaction temperatures than typically taught in the art, specifically temperatures of above 80° C. However, the art teaches away from running at higher temperatures due to undesirable effects including poor catalyst activity, increased polymer formation and increased selectivity towards 1-hexene.

Surprisingly, the catalysts of the present invention are found to be active and selective towards 1-octene above 80° C. Even more surprisingly, these catalysts are still active and selective towards 1-octene above 90° C. Not wishing to be bound by theory, the catalysts of the present Invention are less susceptible to the thermally induced catalytic decomposition pathways, as discussed by van Leeuwen. However, at still higher temperatures, above 130° C., the catalysts of the present invention are no longer sufficiently active or selective towards 1-octene.

Furthermore, it was found that higher reaction temperatures reduced the molecular weight of the polymer co-product. For a tetramerisation process performed at higher reaction temperatures, the lower molecular weight of the polymer co-product will improve the processability of this material downstream of the reactor, for example in flash vessels as described in WO 2011/045701. In addition, any fouling of process equipment by a lower molecular weight polymer co-product may be easier, cheaper and less time-consuming to clean, for example by hot-washing.

The reduced risk of fouling, the potentially simpler and lower cost process design and the improved polymer processability would make a high temperature, solution phase tetramerisation process highly advantageous.

Suitable reaction pressures are from atmospheric to 800 atmospheres (bar), or from 5 atmospheres to 100 atmospheres, or from 40 to 100 atmospheres, or from 60 to 100 atmospheres. It was demonstrated that the negative effect of higher reaction temperatures on selectivity towards 1-octene can be reversed through the use of higher reaction pressures, together with the catalysts and reaction temperature ranges of the present invention.

There exist a number of options for the tetramerisation reactor including batch, semi-batch, and continuous operation. In some embodiments the process is a continuous process, in which case reactors utilizing both CSTR and plug flow behavior may be considered. There are different potential configurations as a subset of these two types of reactors. For example, CSTR type reactors include bubble columns, stirred tanks, loop reactors with single or two phases while plug flow reactors include fixed bed and homogeneous tubular types of varying residence times. As a further subset, reactors can be configured with different cooling options such as internal or external heat exchangers, interstage coolers, and cold feed heat removal amongst others. All configurations can be run in continuous or batch mode, and there is opportunity to configure the same reactor several times in series or use combinations of different reactor types and cooling techniques together to achieve the desired result.

For systems where tetramerisation takes place in the liquid phase, different mass transfer opportunities exist including jet loop mixing, bubble column sparging, tubular reactor multiple injections and pre-saturation of the feed material amongst others.

The reactor type selected may depend on factors such as heat removal, mechanical robustness with regard to fouling, residence time distributions, product composition effects as a result of secondary reactions and mechanical equipment cost implications. In a process where polymer precipitates out of the reaction medium, the selection criteria of heat removal and mechanical robustness with regard to fouling may be expected to dominate and many reactor configurations may therefore be excluded. In a solution phase process, a wider range of reactor configurations may be considered and implemented to optimize factors such as residence time distributions, product composition effects as a result of secondary reactions and mechanical equipment cost implications. In particular, the use of reactors wherein reaction cooling is effected by means of heat exchangers in contact with the reaction medium may be practical in a solution phase process, whereas the susceptibility of such heat exchangers to fouling may rule out such options for a slurry-phase process.

Catalyst Performance

The catalysts of the present invention can operate at higher temperatures with good catalyst activity, while maintaining acceptable selectivities towards 1-octene and low levels of polymer formation. In some embodiments of the invention the average activity of these catalysts is greater than 700 000 g/gCr/h at 100° C., 45 bar, greater than 1 000

000 g/gCr/h at 100° C., 45 bar, or greater than 2 000 000 g/gCr/h at 100° C., 45 bar, or greater than 3 000 000 g/gCr/h at 100° C., 45 bar.

In some embodiments the catalyst produces at least 35 mass % 1-octene at 100° C., 45 bar ethylene, or at least 45 mass % 1-octene at 100° C., 45 bar ethylene. In some embodiments the catalyst produces less than 4 mass % polymer co-product, or less than 3 mass % polymer co-product, or less than 2 mass % polymer co-product.

The invention will now be described in more detail, by way of example only, with reference to the following non-limiting examples.

EXAMPLES

The following abbreviations are used in the examples:
PCl chlorophosphine
Et ethyl
iPr isopropyl
iBu isobutyl
nBu normal-butyl
1,2-DMP 1,2-dimethylpropyl
nHex normal hexyl
Ph phenyl
PNH phosphinoamine, e.g. Ar$_2$PN(R)H, where Ar is an aryl, and R is an organyl group
PNP bis phosphinoamine, e.g. Ar$_2$PN(R)PAr$_2$, where Ar is an aryl, and R is an organyl group
2-FPh ortho-fluorophenyl
DCM Dichloromethane
THF Tetrahydrofuran
TMP 2,2,4-Trimethylpentane
MCH methylcyclohexane
MMAO-3A An aluminoxane product

General Experimental Conditions for Ligand Synthesis

All reactions were carried out under an argon atmosphere using a dual vacuum/nitrogen line and standard Schlenk techniques. Solvents were purified via a Braun solvent purification system All reagents purchased from commercial suppliers were used without further purification. NMR spectra were recorded on a Varian 400 MHz spectrometer using CDCl$_3$. PNP compounds below were prepared by modification of the procedure described in *Synthesis*, 2007, 24, 3863.

Preparation of 2-fluorophenylmagnesium Bromide; (2-FPh)MgBr

A dry and argon flushed Schlenk was charged with iPrMgCl.LiCl (1.42 g, 7.5 mmol, 1.3 M solution in THF). The solution was cooled in an ice bath and 1-bromo-2-fluorobenzene (1.31 g, 7.5 mmol) was added dropwise. The reaction mixture was stirred for 1 hr and the resulting Grignard product was used in the next step as described below.

Preparation of (2-fluorophenyl)$_2$phosphinechloride; (2-FPh)$_2$PCl

The Grignard reagent 2-FPhMgBr (from above) was slowly added to a cooled (−78° C.) solution of PCl$_3$ (0.52 g, 3.8 mmol) in anhydrous THF (10 ml). After addition was complete, the suspension was stirred at room temperature for a further 1 h after which the reaction was complete as judged by $^{31}$P NMR (δ 61.1 (t, J=64.5 Hz). The product was used in the next step without isolation.

Preparation of (2-fluorophenyl)(phenyl)$_2$phosphinechloride; (2-FPh)$_2$PCl The same method as described above was used, except that 1 equivalent of the 2-fluorophenyl Grignard was added to PhPCl$_2$ (instead of PCl$_3$). $^{31}$P NMR (CDCl$_3$): δ 71.2 (d, J=66.0 Hz).

Preparation of 1-Bromo-8-fluoronaphthalene

1-Bromo-8-fluoronaphthalene was prepared as described in Tetrahedron Letters., Vol. 48, pp. 5539-5541, 2007 by Repine. J. T. et. al.

Preparation of 8-fluoronaphth-1-ylmagnesium bromide

1-Bromo-8-fluoronaphthalene (1.5 g, 6.7 mmol) was added to a mixture of magnesium turnings (0.18 g, 7.3 mmol) and 1 iodine crystal in anhydrous THF (20 ml). A vigorous reaction ensued. Stirring was continued at room temperature until all the magnesium had dissolved. Once the reaction exotherm had dissipated, the reaction mixture was heated under reflux for about 15 minutes to yield the required Grignard reagent which was used in the next step as described below.

Preparation of (8-fluoronaphth-1-yl)(phenyl)phosphinechloride 8-fluoronaphth-1-ylmagnesium bromide (separated from excess Mg) was incrementally added to a solution of PhPCl$_2$ (0.9 ml, 6.7 mmol) in anhydrous THF (30 ml) at −78° C. After addition was complete, the suspension was stirred at room temperature for a further 15 min after which the reaction was complete as judged by $^{31}$P NMR. The product was used in the next step without isolation. $^{31}$P NMR (CDCl$_3$): δ 85.75 (d, J=292.10 Hz), 81.44 (d, J=277.84 Hz). (2× d, corresponding to P-Cl and P-Br).

Ligand Preparation Example 1

Preparation of (2-fluorophenyl)$_2$PN(iPr)PPh$_2$ iPrNH$_2$ (0.5 g, 8.46 mmol) and Et$_3$N (1.71, 16.9 mmol) were added to the crude (2-FPh)$_2$PCl compound (1.81 g, 7.1 mmol) [prepared as described above] in diethyl ether (10 ml). The reaction mixture was stirred at room temperature until complete formation of the PNH intermediate. The volatiles were removed in vacuo. Ether (50 ml) was added and the resultant mixture filtered to give the ether solution of the desired PNH product in reasonable purity [by $^{31}$P NMR analysis: δ 15.7 (t, J=33.4 Hz)]. The solvent was evaporated off to give the PNH molecule (0.8 g, 2.9 mmol) which was re-dissolved in DCM (10 ml). Et$_3$N (0.56 g, 5.9 mmol) was added followed by incremental addition of Ph$_2$PCl (1.3 g, 5.9 mmol) at room temperature. After complete conversion of the PNH (judged by $^{31}$P NMR analysis) to the PNP, the volatiles were removed in vacuo. Ether (100 ml) was added and the resultant mixture was filtered through a short activated alumina column. Filtration was repeated until a pure compound was obtained. The solvent was evaporated to give the desired PNP product. $^1$H NMR (CDCl$_3$): δ 7.49-6.82 (m, 18H, Ar), 3.79 (m, 1H, CH), 1.10 (d, 6H, J=6.8 Hz, CH$_3$).

$^{19}$F NMR (CDCl$_3$): δ 103.2 (d, J=49.0 Hz). $^{31}$P NMR (CDCl$_3$): δ 52.5 (br s), 22.6 (br s).

Ligand Preparation Example 2

Preparation of (2-fluorophenyl)$_2$PN(iBu)PPh$_2$

This compound was prepared following the procedure described in ligand example 1 above, except that iBuNH$_2$ instead of iPrNH$_2$ was used. $^1$H NMR (CDCl$_3$): δ 7.45-6.91 (m, 18H, Ar), 3.27 (m, 2H, CH$_2$), 1.21 (m, 1H, CH), 0.58 (d, 6H, J=6.8 Hz, CH$_3$). $^{31}$P NMR (CDCl$_3$): δ 63.2 (br s, PPh2), 39.0 (m, P(2-fluorophenyl)$_2$).

Ligand Preparation Example 3

Preparation of (2-fluorophenyl)$_2$PN(nBu)PPh$_2$

This compound was prepared following the procedure described in ligand example 1 above, except that nBuNH$_2$ instead of iPrNH$_2$ was used. $^1$H NMR (CDCl$_3$): δ 7.45-6.93 (m, 18H, Ar), 3.31 (m, 2H, CH$_2$), 1.21 (m, 1H, CH), 0.58 (d, 6H, J=6.8 Hz, CH$_3$). $^{31}$P NMR (CDCl$_3$): δ 63.2 (d, J=41.6 Hz), 39.0 (m).

Ligand Preparation Example 4

Preparation of (2-fluorophenyl)(Ph)PN(iPr)PPh$_2$

This compound was prepared following the procedure described in ligand example 1 above, except that (2-FPh)PhPCl instead of (2-FPh)$_2$PCl was used. $^1$H NMR (CDCl$_3$): δ 7.61-6.92 (m, 18H, Ar), 3.76 (m, 1H, CH), 1.28 (d, 3H, J=6.4 Hz, CH$_3$), 1.02 (d, 3H, J=6.4 Hz, CH$_3$). $^{31}$P NMR (CDCl$_3$): δ 51.1 (br s), 35.7 (br s).

Ligand Preparation Example 5

Preparation of (2-fluorophenyl)$_2$PN(nBu)P(2-fluorophenyl)$_2$

To a DCM solution (5 ml) of nBuNH$_2$ (0.5 g, 6.9 mmol) and Et$_{3N}$ (2.4 ml, 17.1 mmol) was added (2-FPh)$_2$PCl (3.9 g, 15.05 mmol) [prepared as described above] at room temperature. The reaction was left to stir for 2 hours. After complete conversion of the (2-FPh)$_2$PCl (judged by $^{31}$P NMR analysis) to the PNP, the volatiles were removed in vacuo. The residue was re-slurried in ether (100 ml), followed by filtration of the solids and removal of the solvent in vacuo. $^{31}$P NMR revealed quantitative conversion to the desired product as a clear oil. $^1$H NMR (CDCl$_3$): δ 7.96-7.50 (ArH, m, 16 H), 3.99 (m, CH$_3$CH$_2$CH$_2$CH$_2$N, 2H), 1.72 (m, CH$_3$CH$_2$CH$_2$CH$_2$N, 2H), 1.51 (m, CH$_3$CH$_2$CH$_2$CH$_2$N, 2H), 1.17 (t, CH$_2$CH$_2$CH$_2$CH$_2$N, 3H, J=7.6 Hz). $^{19}$F NMR (CDCl$_3$): δ −103.0 (d, J=53.6 Hz). $^{31}$P NMR (CDCl$_3$): δ 39.2 (m).

Ligand Preparation Example 6

Preparation of (2-fluorophenyl)$_2$PN(nHex)PPh$_2$

This compound was prepared following the procedure described in ligand example 1 above, except that nHexNH$_2$ instead of iPrNH$_2$ amine was used. $^{31}$P NMR (CDCl$_3$):.δ 3.38 (d, J=41.47 Hz), 40.39 (m).

Ligand Preparation Example 7

Preparation of (8-fluoronaphth-1-yl)PhPN(nBu)PPh$_2$ nBuNH$_2$ (0.5 g, 6.24 mmol) and Et$_3$N (1.74 ml, 12.5 mmol) were added to the crude (8-fluoronaphth-1-yl)(phenyl)phosphinechloride (1.5 g, 5.2 mmol) [prepared as described above] in diethyl ether (50 ml). The reaction mixture was stirred at room temperature until complete formation of the PNH intermediate. The volatiles were removed in vacuo. Ether (50 ml) was added and the resultant mixture filtered to give the ether solution of the desired PNH product in reasonable purity [by $^{31}$P NMR analysis: δ 41.93 (d, J=201.81 Hz)]. The solvent was evaporated off to give the PNH molecule (0.8 g, 2.5 mmol) which was re-dissolved in DCM (10 ml). Et$_3$N (0.69 ml, 5.0 mmol) was added followed by incremental addition of Ph$_2$PCl (0.5 ml, 2.5 mmol) at room temperature. After complete conversion of the PNH (judged by $^{31}$P NMR analysis) to the PNP, the volatiles were removed in vacuo. Ether (100 ml) was added and the resultant mixture was filtered through a short activated alumina column. Filtration was repeated until a pure compound was obtained. The solvent was evaporated to give the desired PNP product. $^1$H NMR (CDCl$_3$): δ 7.78-6.88 (m, 21H, Ar), 3.29 (m, 2H, CH$_2$), 1.28 (m, 1H, CH$_2$), 0.83 (m, 3H, CH$_2$), 0.55 (t, 3H, CH$_3$, J=7.80 Hz). $^{19}$F NMR (CDCl$_3$): δ 101.7 (d, J=205.73 Hz). $^{31}$P NMR (CDCl$_3$): δ 64.00 (dd, J=205.86 and J=43.68 Hz), 62.64 (br s).

Ligand Preparation Comparative Example 1

Preparation of Ph$_2$PN(iPr)PPh$_2$

This compound was prepared from the reaction of iPrNH$_2$ (1.0 g, 16.9 mmol), Et$_3$N (3.4 g, 33.8 mmol), Ph$_2$PCl (7.4 g, 33.8 mmol) in DCM, following a procedure described in *Synthesis*, 2007, 24, 3863. $^{31}$P NMR (CDCl$_3$): δ 48.2 (s).

Ligand Preparation Comparative Example 2

Preparation of Ph$_2$PN(iBu)PPh$_2$

This compound was prepared from the reaction of iBuNH$_2$ (1.0 g, 13.7 mmol), Et$_3$N (5.54 g, 54.7 mmol), Ph$_2$PCl (7.59 g, 41.0 mmol), following a procedure described in *Synthesis*, 2007, 24, 3863. $^{31}$P NMR (CDCl$_3$): δ 62.8 (s).

Ligand Preparation Comparative Example 3

Preparation of (1-naphthyl)$_2$PN(nBu)PPh$_2$

To an ether solution (10 ml) of nBuNH$_2$ (0.35 g, 4.69 mmol) was added ClP(1-naphthyl)$_2$ (0.5 g, 1.56 mmol) and Et$_3$N (0.45 g, 4.70 mmol). The reaction mixture was left to stir for 2 hrs followed by filtration of the solids and removal of the solvent to give the PNH molecule (1-naphthyl)$_2$PN(nBu)H. $^{31}$P NMR (CDCl$_3$): δ 25.6 (s). The PNH molecule (1-naphthyl)$_2$PN(nBu)H (0.4 g, 1.12) was treated with Et$_3$N (0.34 g, 3.36 mmol) and ClPPh$_2$ (0.49 g, 2.23 mmol) to give the desired PNP, following a procedure described in *Synthesis*, 2007, 24, 3863.

$^{31}$P NMR (CDCl$_3$): δ 63.4 (d, J=79.1 Hz), 48.6 (d, J=79.1 Hz).

Ligand Preparation Comparative Example 4

Preparation of Ph$_2$PN(nBu)PPh$_2$

This compound was prepared from the reaction of nBuNH$_2$ (1.0 g, 13.7 mmol), Et$_3$N (5.54 g, 54.7 mmol), Ph$_2$PCl (7.59 g, 41.0 mmol), following a procedure described in *Synthesis*, 2007, 24, 3863. $^{31}$P NMR (CDCl$_3$): δ 62.5 (s).

Example 1

Ethylene tetramerisation with (2-fluorophenyl)$_2$PN(iPr)PPh$_2$ at 100° C. and 45 bar A 600 ml stainless steel reactor was heated to 120° C. for 30 minutes under vacuum, backfilled with N$_2$ and then cooled to 60° C. The reactor was charged with 2,2,4-trimethylpentane (TMP) (100 ml), and heated to 90° C. Separately, MMAO-3A (2.4 mmol Al) was added to a mixture of Cr(acac)$_3$ (2.5 μmol) and (2-fluorophenyl)$_2$PN(iPr)PPh$_2$ (2.5 μmol) in cyclohexane (5 ml). This mixture was then transferred to the reactor. The reactor was pressurised with ethylene (45 bar), and stirred (1300 r.p.m.) with a gas entraining stirrer. The temperature in the reactor increased to 100° C., at which point the reactor was cooled by means of an internal cooling coil to maintain a constant temperature of 100° C. throughout the run. The reaction pressure was kept constant throughout the run by feeding ethylene on demand, and the consumption of ethylene was monitored via a flow meter. At the conclusion of the run after 12 minutes and 200 g total ethylene uptake (including the ethylene required to pressurise the reactor), the reactor was rapidly cooled to 5° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Example 2

Ethylene tetramerisation with (2-fluorophenyl)$_2$PN(iBu)PPh$_2$ at 100° C. and 45 bar The procedure of example 1 was followed, except that 200 ml TMP was used, the ligand (2-fluorophenyl)$_2$PN(iBu)PPh$_2$ was used, and the reaction was terminated after 40.4 minutes and 150 g ethylene uptake (including the ethylene required to pressurise the reactor). The results are shown in Table 1.

Example 3

Ethylene tetramerisation with (2-fluorophenyl)$_2$PN(nBu)PPh$_2$ at 100° C. and 45 bar The procedure of example 1 was followed, except the ligand (2-fluorophenyl)$_2$PN(nBu)PPh$_2$ was used, and the reaction was terminated after 35.0 minutes and 160 g ethylene uptake (including the ethylene required to pressurise the reactor). The results are shown in Table 1.

Example 4

Ethylene tetramerisation with (2-fluorophenyl)(Ph)PN(iPr)PPh$_2$ at 100° C. and 45 bar The procedure of example 1 was followed, except that 200 ml TMP was used, the ligand (2-fluorophenyl)(Ph)PN(iPr)PPh$_2$ was used, and the reaction was terminated after 27.2 minutes and 150 g ethylene uptake (including the ethylene required to pressurise the reactor). The results are shown in Table 1.

Example 5

Ethylene tetramerisation with (2-fluorophenyl)$_2$PN(nBu)P(2-fluorophenyl)$_2$ at 95° C. and 55 bar The procedure of example 1 was followed, except that 200 ml TMP was used, the ligand (2-fluorophenyl)$_2$PN(nBu)P(2-fluorophenyl)$_2$ was used, and the reaction was terminated after 7 minutes and 150 g ethylene uptake (including the ethylene required to pressurise the reactor). The results are shown in Table 1.

Example 6

Ethylene tetramerisation with (8-fluoronaphth-1-yl)(Ph)PN(nBu)PPh$_2$ at 100° C. and 45 bar The procedure of example 1 was followed, except that 200 ml methylcyclohexane (MCH) was used, the ligand (8-fluoronaphth-1-yl)(Ph)PN(nBu)PPh$_2$ was used, and the reaction was terminated after 27.5 minutes and 140 g ethylene uptake (including the ethylene required to pressurise the reactor). The results are shown in Table 1.

Example 7

Ethylene tetramerisation with (8-fluoronaphth-1-yl)(Ph)PN(nBu)PPh$_2$ at 90° C. and 60 bar The procedure of example 1 was followed, except that 200 ml TMP was used, the ligand (8-fluoronaphth-1-yl)(Ph)PN(nBu)PPh$_2$ was used, and the reaction was terminated after 21.3 minutes and 150 g ethylene uptake (including the ethylene required to pressurise the reactor). The results are shown in Table 1.

Example 8

Ethylene tetramerisation with (2-fluorophenyl)(Ph)PN(iPr)PPh$_2$ at 100° C. and 70 bar (TEA/Perfluoroaluminate Activator)

A 1200 ml stainless steel reactor was heated to 120° C. for 30 minutes under vacuum, backfilled with N$_2$ and then cooled to 60° C. The reactor was charged with methylcyclohexane (200 ml), AlEt$_3$ (462.5 μmol) and ZnEt$_2$ (125 μmol), and heated to 90° C. Separately, [(C$_{18}$H$_{37}$)$_2$(CH$_3$)NH][Al(OC{CF$_3$}$_3$)$_4$](1.5 μmol) in methylcyclohexane) was added to a mixture of Cr(2-ethylhexanoate)$_3$ (1.25 μmol) and (2-fluorophenyl)(Ph)PN(iPr)PPh$_2$ (1.5 µmol) in methylcyclohexane, then triethylaluminium (62.5 µmol) in methylcyclohexane (2 ml) was added and the mixture stirred for 1 minute. This mixture was then transferred to the reactor. The reactor was pressurised with ethylene (70 bar), and stirred (1300 r.p.m.) with a gas entraining stirrer. The temperature in the reactor increased to 100° C., at which point the reactor was cooled by means of an internal cooling coil to maintain a constant temperature of 100° C. throughout the run. The reaction pressure was kept constant throughout the run by feeding ethylene on demand, and the consumption of ethylene was monitored via a flow meter. At the conclusion of the run after 63 minutes and 470 g total ethylene uptake (including the ethylene required to pressurise the reactor), the reactor was rapidly cooled to 5° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Comparative Example 1

Ethylene tetramerisation with Ph$_2$PN(iPr)PPh$_2$ at 100° C. and 45 bar

The procedure of example 1 was followed, except that 200 ml TMP was used, the ligand Ph$_2$PN(iPr)PPh$_2$ was used and the reaction was terminated after 40 minutes and 65.9 g ethylene uptake (including the ethylene required to pressurise the reactor). The results are shown in Table 1.

Comparative example 2

Ethylene tetramerisation with Ph$_2$PN(iBu)PPh$_2$ at 100° C. and 45 bar

The procedure of example 1 was followed, except that 200 ml TMP was used, the ligand Ph$_2$PN(iBu)PPh$_2$ was used, and the reaction was terminated after 27 minutes and 59.6 g ethylene uptake (including the ethylene required to pressurise the reactor). The results are shown in Table 1.

Comparative example 3

Ethylene tetramerisation with (1-naphthyl)$_2$PN(nBu)PPh$_2$ at 100° C. and 45 bar The procedure of example 1 was followed, except that 200 ml TMP was used, the ligand (1-naphthyl)$_2$PN(nBu)PPh$_2$ was used, and the reaction was terminated after 30 minutes and 46.1 g ethylene uptake (including the ethylene required to pressurise the reactor). The results are shown in Table 1.

Example 9

Ethylene tetramerisation with (2-fluorophenyl)$_2$PN(nBu)PPh$_2$ at 90° C. and 45 bar A 2000 ml stainless steel reactor was heated to 120° C. for 30 minutes under vacuum, backfilled with N$_2$ and then cooled to 60° C. The reactor was charged with methylcyclohexane (MCH) (185 ml). When the targeted operation temperature of 90° C. had been achieved, and while stirring with a gas-entraining stirrer, 1 bar H$_2$ partial pressure was added to the reactor. The reactor was then pressurised with ethylene to 40 bar. Separately, MMAO-3A (4.8 mmol Al) was added to a mixture of Cr(acac)$_3$ (5.0 µmol) and (2-fluorophenyl)$_2$PN(nBu)PPh$_2$ (5.0 µmol) in cyclohexane (total volume of 15 ml). This mixture was then transferred to a burette attached to the reactor. The burette was pressurised with ethylene at 45 bar, and the catalyst mixture was immediately transferred into the reactor by opening the port between the reactor and the burette. After reaction commenced, the reactor was cooled by means of an internal cooling coil to maintain a constant temperature of 90° C. throughout the run. The reaction pressure was kept constant at 45 bar throughout the run by feeding ethylene on demand, and the consumption of ethylene was monitored via a flow meter. At the conclusion of the run after 7.5 minutes and 220 g ethylene uptake (excluding the ethylene required to pressure the reactor to 40 bar), the reactor was rapidly cooled to 15° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Example 10

Ethylene tetramerisation with (2-fluorophenyl)$_2$PN(nBu)PPh$_2$ at 100° C. and 45 bar The procedure of example 9 was followed, except that the reaction temperature was 100° C., and the reaction was terminated after 11.7 minutes and 220 g ethylene uptake. The results are shown in Table 1.

Example 11

Ethylene tetramerisation with (2-fluorophenyl)$_2$PN(nBu)PPh$_2$ at 105° C. and 45 bar The procedure of example 9 was followed, except that the reaction temperature was 105° C., and the reaction was terminated after 29.7 minutes and 220 g ethylene uptake. The results are shown in Table 1.

Example 12

Ethylene tetramerisation with (2-fluorophenyl)$_2$PN(nHex)PPh$_2$ at 115° C. and 75 bar The procedure of example 9 was followed, except that the reactor was pre-pressurised to 70 bar, the ligand (2-fluorophenyl)$_2$PN(nHex)PPh$_2$ was used, the reaction temperature was 115° C., the reaction pressure was 75 bar, and the reaction was terminated after 12 minutes and 83 g ethylene uptake. The results are shown in Table 1.

Example 13

Ethylene tetramerisation with (2-fluorophenyl)$_2$PN(nHex)PPh$_2$ at 100° C. and 75 bar The procedure of example 9 was followed, except that the reactor was pre-pressurised to 70 bar, the ligand (2-fluorophenyl)$_2$PN(nHex)PPh$_2$ was used, the reaction temperature was 100° C., the reaction pressure was 75 bar, and the reaction was terminated after 5.7 minutes and 220 g ethylene uptake. The results are shown in Table 1.

Comparative Example 4

Ethylene tetramerisation with Ph$_2$PN(nBu)PPh$_2$ at 90° C. and 45 bar

The procedure of example 9 was followed, except that the ligand Ph$_2$PN(nBu)PPh$_2$ was used, the reaction temperature was 90° C., and the reaction was terminated after 40.0 minutes and 145.6 g ethylene uptake. The results are shown in Table 1.

TABLE 1

Catalytic results to demonstrate the present invention

| Ex. | Ligand | Temp (° C.), Press (bar) | Activity (×10$^6$ g/gCr/h) | 1-Hexene selectivity (mass %) | 1-Octene selectivity (mass %) | Polymer selectivity (mass %) | 1-Octene:1-Hexene ratio (g/g) |
|---|---|---|---|---|---|---|---|
| 1 | (2-FPh)$_2$PN(iPr)PPh$_2$ | 100, 45 | 5.3 | 48.2 | 35.8 | 0.9 | 0.74 |
| 2 | (2-FPh)$_2$PN(iBu)PPh$_2$ | 100, 45 | 1.7 | 45.3 | 38.8 | 2.4 | 0.85 |
| 3 | (2-FPh)$_2$PN(nBu)PPh$_2$ | 100, 45 | 1.7 | 33.2 | 46.7 | 2.1 | 1.40 |
| 4 | (2-FPh)(Ph)PN(iPr)PPh$_2$ | 100, 45 | 1.9 | 56.0 | 30.2 | 1.3 | 0.54 |
| 5 | (2-FPh)$_2$PN(nBu)P(2-FPh)$_2$ | 95, 55 | 6.6 | 45.3 | 43.1 | 3.5 | 0.95 |
| 6 | (8-F-Naphth-1-yl)(Ph)PN(nBu)PPh$_2$ | 100, 45 | 1.5 | 40.4 | 37.4 | 2.2 | 0.93 |
| 7 | (8-F-Naphth-1-yl)(Ph)PN(nBu)PPh$_2$ | 90, 60 | 1.8 | 25.3 | 48.3 | 1.2 | 1.91 |
| 8 | (2-FPh)(Ph)PN(iPr)PPh$_2$ | 100, 70 | 4.5 | 51.1 | 37.7 | 2.7 | 0.74 |
| Comp 1 | Ph$_2$PN(iPr)PPh$_2$ | 100, 45 | 0.5 | 46.0 | 40.0 | 3.2 | 0.89 |
| Comp 2 | Ph$_2$PN(iBu)PPh$_2$ | 100, 45 | 0.3 | 30.3 | 51.2 | 3.6 | 1.69 |
| Comp 3 | (1-Naphth)$_2$PN(nBu)PPh$_2$ | 100, 45 | 0.1 | 17.2 | 20.3 | 52.7 | 1.18 |
| 9 | (2-FPh)$_2$PN(nBu)PPh$_2$ | 90, 45 | 8.5 | 25.4 | 50.2 | 2.5 | 1.98 |
| 10 | (2-FPh)$_2$PN(nBu)PPh$_2$ | 100, 45 | 4.3 | 31.1 | 45.2 | 6.1 | 1.45 |
| 11 | (2-FPh)$_2$PN(nBu)PPh$_2$ | 105, 45 | 1.6 | 33.9 | 37.4 | 12.4 | 1.10 |
| 12 | (2-FPh)$_2$PN(nHex)PPh$_2$ | 115, 75 | 1.9 | 42.0 | 32.0 | 11.8 | 1.31 |
| 13 | (2-FPh)$_2$PN(nHex)PPh$_2$ | 100, 75 | 12.6 | 22.8 | 54.1 | 4.7 | 2.37 |
| Comp 4 | Ph$_2$PN(nBu)PPh$_2$ | 90, 45 | 0.7 | 18.5 | 50.9 | 6.8 | 2.76 |

The invention claimed is:

1. A process for the tetramerisation of ethylene, the process including:
   (a) providing an activated catalyst comprising:
      i) a source of chromium;
      ii) a ligating compound of the formula
         R$^1$R$^2$P$^1$XP$^2$R$^3$R$^4$
         wherein P$^1$ and P$^2$ are phosphorus atoms;
         X is a linking group between P$^1$ and P$^2$; and
         R$^1$ to R$^4$ are independently a hydrocarbyl group, an organoheteryl group or a heterohydrocarbyl group, wherein at least one of R$^1$, R$^2$, R$^3$, and R$^4$ contains a fluorine substituent; and
      iii) optionally a catalyst activator or combination of catalyst activators; and
   (b) contacting ethylene to be tetramerised with the activated catalyst at a reaction temperature of from above 80° C. to about 130° C.

2. A process according to claim 1, wherein the ethylene is contacted with the activated catalyst at a reaction temperature of from above 85° C. to about 120° C.

3. A process according to claim 1, wherein the ethylene is contacted with the activated catalyst at a reaction temperature of from above 90° C. to about 110° C.

4. A process according to claim 1, wherein at least one of R$^1$ to R$^4$ is an aromatic moiety or a heteroaromatic moiety directly bonded to P$^1$ or P$^2$.

5. A process according to claim 1, wherein R$^1$ to R$^4$ are all aromatic or heteroaromatic moieties directly bonded to P$^1$ or P$^2$.

6. A process according to claim 1, wherein R$^1$ to R$^4$ are optionally substituted phenyl groups.

7. A process according to claim 1, wherein one or more of the R$^1$ to R$^4$ groups containing a fluorine substituent are aromatic or heteroaromatic moieties directly bonded to P$^1$ or P$^2$ and containing a fluorine atom or a fluorinated substituent at a ring atom of the aromatic ring structure that is no more than two atoms away along the shortest connecting path from the ring atom bound to P$^1$ or P$^2$.

8. A process according to claim 1, wherein one or more of the R$^1$ to R$^4$ groups containing a fluorine substituent are aromatic or heteroaromatic moieties directly bonded to P$^1$ or P$^2$ and containing a fluorine atom at a ring atom of the aromatic ring structure that is no more than two atoms away along the shortest connecting path from the ring atom bound to P$^1$ or P$^2$.

9. A process according to claim 1, wherein one or more of the R$^1$ to R$^4$ groups containing a fluorine substituent are groups containing aromatic or heteroaromatic moieties separated from P$^1$ or P$^2$ by a single atom linker, and which contain a fluorine atom or a fluorinated substituent at a ring atom of the aromatic ring structure that is no more than two atoms away along the shortest connecting path from the ring atom bound to the single atom linker.

10. A process according to claim 1, wherein one or more of the R$^1$ to R$^4$ groups containing a fluorine substituent are aromatic moieties directly bonded to P$^1$ or P$^2$ and containing a fluorine atom or fluorinated substituent at a ring atom of the aromatic ring structure that is adjacent to the ring atom bound to P$^1$ or P$^2$.

11. A process according to claim 1, wherein one or more of the R$^1$ to R$^4$ groups containing a fluorine substituent are optionally substituted 2-fluorophenyi groups.

12. A process according to claim 1, wherein no more than two of R$^1$ to R$^4$ are aromatic or heteroaromatic moieties directly bonded to P$^1$ or P$^2$ and containing a fluorine atom or a fluorinated substituent at a ring atom of the aromatic ring structure that is no more than two atoms away along the shortest connecting path from the ring atom bound to $P^1$ or $P^2$.

13. A process according to claim 1, wherein $R^1$ and $R^2$ both are aromatic selected from heteroaromatic moieties directly bonded to $P^1$ or $P^2$ and containing a fluorine atom or a fluorinated substituent at a ring atom of the aromatic ring structure that is no more than two atoms away along the shortest connecting path from the ring atom bound to $P^1$ or $P^2$.

14. A process according to claim 1, wherein X is —N($R^9$)—, where $R^9$ is a hydrocarbyl group, a heterohydrocarbyl group or an organoheteryl group.

15. A process according to claim 1, wherein the process is a continuous process.

16. A process according to claim 1, wherein the average activity of the activated catalyst is greater than 700 000 g/gCr/h at 100° C., 45 bar.

17. A process according to claim 1, wherein at least 35 mass % 1-octene is produced.

18. A process according to claim 1, wherein at least 45 mass % 1-octene is produced.

\* \* \* \* \*